United States Patent [19]

Redington

[11] Patent Number: 4,516,582
[45] Date of Patent: May 14, 1985

[54] NMR BLOOD FLOW IMAGING

[75] Inventor: Rowland W. Redington, Schenectady, N.Y.

[73] Assignee: General Electric Company, Schenectady, N.Y.

[21] Appl. No.: 490,605

[22] Filed: May 2, 1983

[51] Int. Cl.³ ............................................. A61B 5/02
[52] U.S. Cl. .................................... 128/653; 324/309
[58] Field of Search ....................... 128/653; 324/309; 378/4

[56] References Cited

U.S. PATENT DOCUMENTS

| | | | |
|---|---|---|---|
| 3,191,119 | 6/1965 | Singer | 325/0.5 |
| 3,809,070 | 5/1974 | Doll et al. | 128/2.05 F |
| 4,037,585 | 7/1977 | Gildenberg | 128/2 A |
| 4,110,680 | 8/1978 | Bergmann et al. | 325/0.5 |
| 4,115,730 | 9/1978 | Mansfield | 324/309 |
| 4,182,173 | 1/1980 | Papadofrangakis et al. | 73/194 |
| 4,205,687 | 6/1980 | White et al. | 128/663 |
| 4,259,638 | 3/1981 | Krueger | 324/306 |
| 4,318,044 | 3/1982 | Mansfield | 324/309 |
| 4,334,543 | 6/1982 | Fehr | 128/663 |
| 4,374,360 | 2/1983 | Sepponen | 324/309 |
| 4,411,012 | 10/1983 | Pfeiler et al. | 378/4 |
| 4,426,715 | 1/1984 | Baer et al. | 378/4 |

OTHER PUBLICATIONS

Cho et al., Fourier Transform Nuclear Magnetic Resonance Tomographic Imaging, Proceedings of the IEEE, vol. 70, No. 10, Oct. 1982, pp. 1152-1173.
Singer, NMR Flow Imaging, Proceedings of an International Symposium on Nuclear Magnetic Resonance Imaging, Oct. 1981, pp. 185-190.
Gore, The Meaning and Significance of Relaxation in NMR Imaging, Proceedings of an International Symposium on Nuclear Magnetic Resonance Imaging, Oct. 1981, pp. 15-23.
Ordidge et al., Real Time Moving Images by NMR, Proceedings of an International Symposium on NMR Imaging, Oct. 1981, pp. 89-92.

Primary Examiner—Kyle L. Howell
Assistant Examiner—Ruth S. Smith
Attorney, Agent, or Firm—Lawrence D. Cutter; James C. Davis, Jr.; Marvin Snyder

[57] ABSTRACT

A method and apparatus for producing two-dimensional, plan view images of in vivo blood flow networks using unique nuclear magnetic resonance (NMR) pulse sequences are disclosed. The method teaches the use of a pair of 90° selective pulses separated by a delay time optimized to provide images with enhanced blood flow contrast by discriminating against stationary media surrounding the blood flow path. For the instant method, two-dimensional images are compiled by the illustrative apparatus using a collection of NMR slice data, wherein each slice reflects a one-dimensional projection of NMR received signal data in a thin planar slab selected to be generally orthogonal to the primary blood flow network. Further alternative embodiments discuss the use of free induction decay (FID) signals, as well as single pulse and multiple pulse spin echo sequences.

19 Claims, 19 Drawing Figures

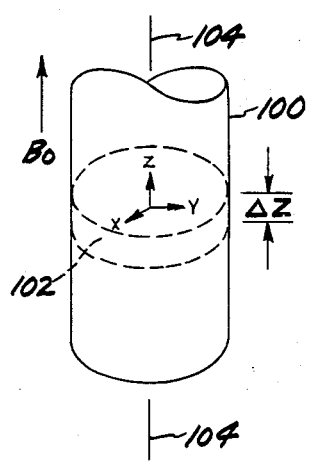
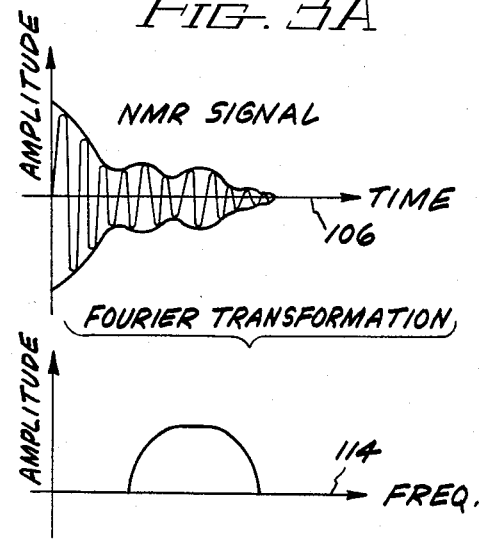
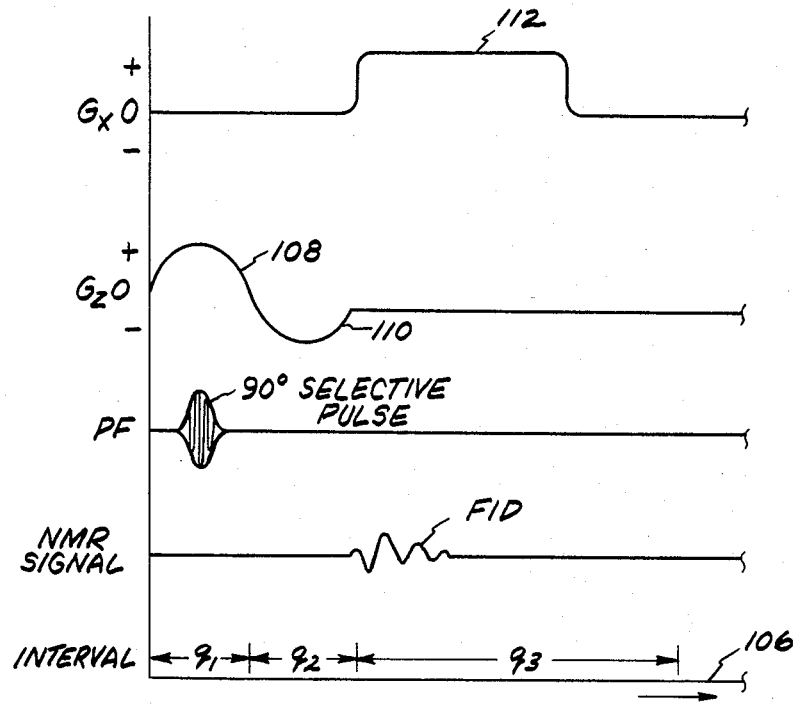

FIG. 7
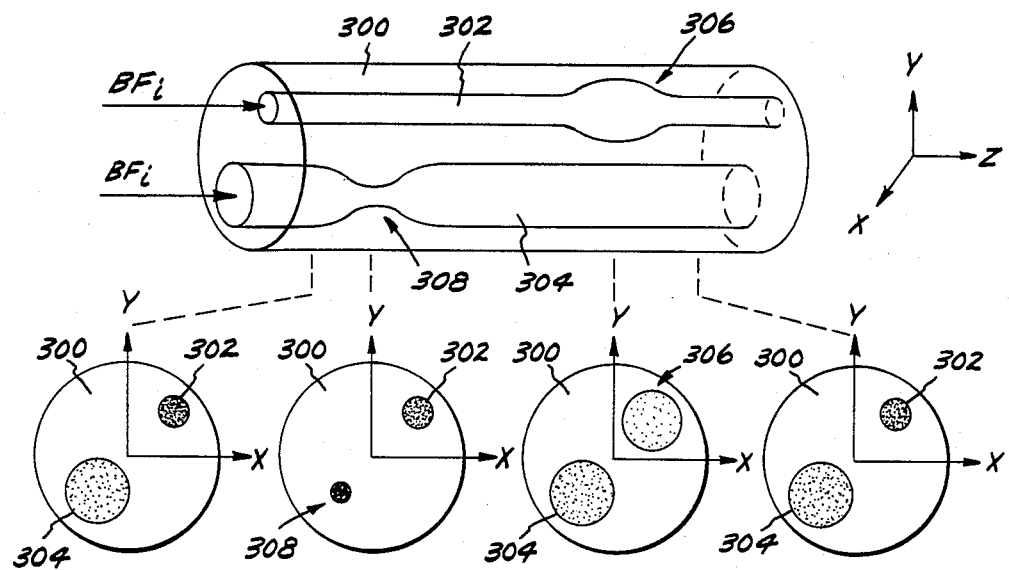
FIG. 7A  FIG. 7C  FIG. 7E  FIG. 7G
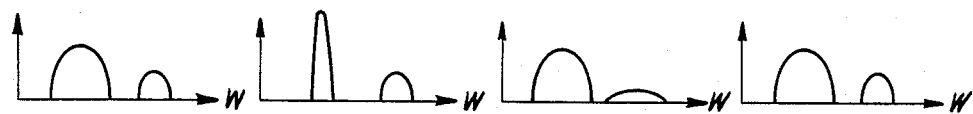
FIG. 7B  FIG. 7D  FIG. 7F  FIG. 7H
FIG. 8
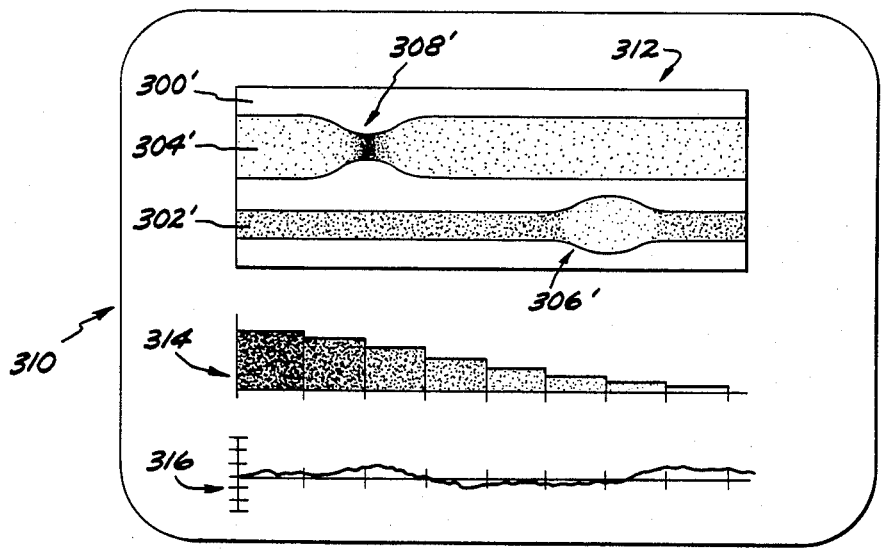

NMR BLOOD FLOW IMAGING

BACKGROUND OF THE INVENTION

The present invention relates generally to the imaging of liquids flowing in heterogeneous objects using nuclear magnetic resonance (NMR) methods. More specifically, the present invention relates to in vivo blood flow imaging wherein image contrast enhancement is achieved by exploiting blood flow rate to discriminate against the stationary media surrounding the blood flow network. In particular, the instant application discloses methods and apparatus for producing a plan view image of blood flow in portions of the human body by providing relative scanning motion between the body portion and the NMR pulse sequencing apparatus to produce particular NMR signal data, and thereafter processing this NMR signal data to produce a flow rate enhanced two dimensional image of the blood flow network.

NMR imaging as a medical diagnostic tool offers significant advantages, the most important of which are the completely non-invasive nature of the technology, and the ability to spatially encode the NMR signal data with a good degree of precision using field gradients. The term Zeugmatography has been coined recently to cover an increasing range of NMR techniques wherein static magnetic fields (to produce the polarization of nuclei) are combined with field gradients (to spatially encode the volume of interest) and with RF fields (to spatially reorient polarized nuclei) to achieve a wide range of objectives, including imaging. In the recent past, the technical and patent literature have burgeoned and have reported results of successive advances in the field. While the field has progressed steadily, certain intrinsic drawbacks have heretofore limited certain uses of NMR high resolution imaging in medicine. Chief among these are the comparatively slow nuclear spin relaxation times of human tissue, and body motion due both to inherent movements within the body and the difficulty of keeping the body stationary for long periods of time. Human tissue is known to have a spinlattice relaxation time, $T_1$, of approximately 0.5 seconds and a spin-spin relaxation time, $T_2$, of approximately 0.05 seconds. Both of these time constants are very slow as compared to the speed of the instrumentation available to process NMR signals. Also, high resolution imaging requires a large number of pixel projections, each of which may be the result of a complete NMR pulse sequence, where each NMR sequence is at least influenced by if not limited by these time constants. Therefore, real time (or even near-real time) imaging of body tissue has been of somewhat limited resolution, or contrast, and two-dimensional plan view maps of moving elements such as blood have not heretofore been considered. High contrast two-dimensional imaging of in vivo blood flow in real time has been beyond the reach of NMR technologies.

Over the years, NMR has been used to measure flow, including flow rates in a variety of fluids as well as blood flow, but not in an imaging context. An early approach to using NMR in general for measuring fluid flow (actually liquid flow) is provided in U.S. Pat. No. 3,191,119 to Singer. This patent discloses the measurement of flow rates basically by measuring the amount of absorption energy needed to restore a transported volume of polarized liquid at a downstream location in a conduit, to the amount of polarization which was induced in an upstream location. While the disclosure recites applicability of the scheme to blood flow, it is clear that the apparatus is not conveniently adoptable to in vivo measurement. The Singer patent is illustrative of a fair sized body of prior art using similar NMR techniques to measure liquid flow generally confined within conduits, around which instrumentation is placed. Recent patents of this genre are U.S. Pat. No. 4,259,638 to Krueger et al. and U.S. Pat. No. 4,110,680 to Bergmann et al.

Producing blood flow images of various sorts also may be found in the patent literature, but these make extensive use of acoustic or other forms of energy. U.S. Pat. No. 4,205,687 to White et al. discloses the production of a color coded television or CRT type display of a portion of a blood vessel obtained using a mechanically articulated transducer to cover the area of interest on the patient. This approach uses basic Doppler processing and produces a velocity/color CRT image. U.S. Pat. No. 4,182,173 to Papadofrangakis et al. and assigned to the instant assignee, also discloses a sonic Doppler technique for imaging portions of the body including blood vessels, and produces a real time measurement of flow velocity in selected regions of the patient. A B-scan CRT display is provided on which cross sectional view data is presented.

A method of measuring in vivo blood flow using hard radiation is described in U.S. Pat. No. 4,037,585 to Gildenberg. The disclosure recites the use of X or gamma ray scanning of the cranium in successive layers or slices by a narrow beam, and the subsequent digital processing of the resultant signals to build up a visual presentation of the slice under examination. Additional non-invasive blood flow measuring techniques are taught in U.S. Pat. No. 3,809,070 to Doll et al., and in U.S. Pat. No. 4,334,543 to Fehr.

Despite the significant amount of effort directed towards the tasks of imaging human tissue in general, and in particular to the imaging of blood, it is clear that the primary features needed for an effective, clinically useful imaging means have eluded previous efforts. The present invention is directed to meeting these needs by providing a non-invasive, in vivo, realtime, high contrast two-dimensional imaging capability using the unique characteristics of particular NMR pulse sequences.

SUMMARY OF THE INVENTION

It is therefore a primary object of the present invention to provide an improved method and apparatus for producing non-invasive, high contrast images of blood flow networks using the special capabilities of NMR technology.

Another object of the present invention is to provide methods and apparatus for producing in vivo, two-dimensional images of blood vessels using particular NMR sequences optimized to enhance the image contrast.

Yet another object of the present invention is to provide methods for producing two-dimensional blood flow image maps using unique NMR pulse sequences directed to enhancing the image contrast by discrimination against the stationary media surrounding the blood flow paths.

In the preferred embodiment, an NMR pulse sequence comprises a pair of 90° selective pulses separated by delay time optimized to provide discrimination against the stationary media surrounding the blood flow network. The images thereby produced are further improved by using a 180° selective pulse after application of the 90° pair of pulses so as to preserve the fine frequency detail available in a complete one-spin echo signal. In the present invention, two-dimensional images are compiled using a collection of contiguous or overlapping NMR slice data, wherein each slice comprises a one-dimensional projection of the NMR received signal data in a planar slab selected to be orthogonal to the major blood flow networks.

BRIEF DESCRIPTION OF THE DRAWINGS

The subject matter which is regarded as the invention is particularly pointed out and distinctly claimed in the concluding portion of the specification. The invention, however, both as to organization and method of practice, together with further objects and advantages thereof, may best be understood by reference to the following description taken in connection with the accompanying drawings, in which:

FIG. 1 illustrates an NMR imaging sample positioned in a static magnetic field and having a thin planar slab defined therein by selective excitation;

FIG. 2 illustrates a basic NMR pulse sequence suitable for one-dimensional imaging of the sample;

FIGS. 3A and 3B show, respectively the free induction decay (FID) signal of FIG. 2 in more detail, and the resulting amplitude versus frequency spectrum of that signal after Fourier transformation;

FIG. 7 is an isometric illustration of a portion of a blood-vessel-carrying body member;

FIGS. 7A–7H illustrate selected cross sections through the body member of FIG. 7 together with their Fourier transformed projections.

FIG. 8 illustrates a CRT display of a typical blood flow image map produced using methods in accordance with the present invention.

DETAILED DESCRIPTION OF THE PREFERRED EMBODIMENTS

Figures 4A, 4B:
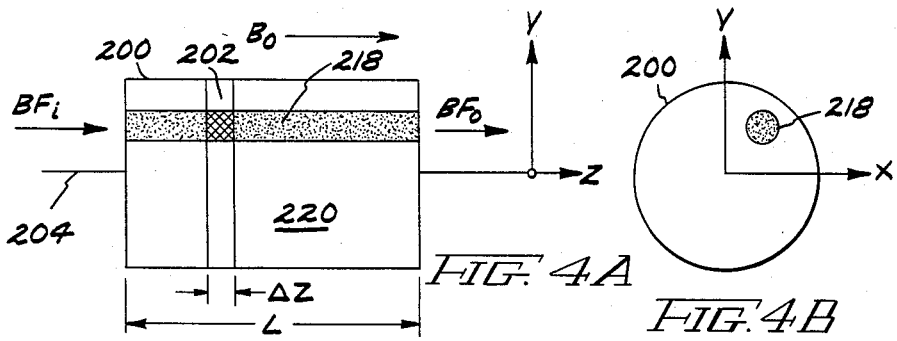
FIGS. 4A and 4B show side and end views respectively of a heterogeneous sample which is to be imaged.

Prior to a description of the actual NMR methods and apparatus employed to practice the present invention, it is instructive to consider the various stages of the imaging process. The three primary stages are: excitation; spatial differentiation; and reconstruction. Major emphasis is placed herein on the first two of these stages during which the most novel features of the present invention come into play. It is also useful at this point to provide a brief overview of the basic NMR method of selective excitation, a modified version of which is advantageously employed in the preferred embodiments of the present invention.

Referring to FIG. 1, there is shown sample 100 positioned in a static homogeneous magnetic field $B_0$ directed along the positive z-axis of a conventional Cartesian coordinate system. The z-axis is selected to be coincident with central axis 104 of cylindrical sample 100. The origin of the coordinate system is taken to be the center of the imaging sample, which is also at the center of a thin planar slab or imaging volume 102 (alternatively designated $\Delta Z$) selected by the selective excitative method as described herein. For the initial purposes of FIG. 1, this coordinate system may be considered as fixed in the laboratory frame of reference. Thereafter, it is more useful and conventional to consider this coordinate system as a rotating system, rotating at the Larmor frequency described below. Typically, the thickness $\Delta Z$ of planar slice 102 is in the range of a few (1-20) mm. The effect of static magnetic field $B_0$ is to polarize nuclear spins in sample 100 having net magnetic moments so that a greater number of nuclear spins align with the $B_0$ field and add together to produce a macroscopic magnetization M (not shown). This polarization allows the resonance phenomenon to occur. Individual polarized nuclear spins, and hence magnetization M, resonate, or precess, about the axis of field $B_0$ at a frequency of precession $\omega$ given by the Larmor equation $$\omega = \gamma B_o \qquad (1)$$

in which $\gamma$ is the gyromagnetic ratio, a precisely known atomic constant for each isotope. The value of $\gamma$ for hydrogen ($^1H$) is about 42.6 MHz/tesla (1 tesla = $10^4$ gauss). $^1H$ is ubiquitous in living tissue and exhibits a stronger NMR signal as compared to other elements in tissue such as nitrogen, phosphorus, carbon and so forth. For this reason, spatial nuclear spin distribution of naturally occurring hydrogen is commonly used in NMR imaging. The static magnetic field $B_0$ is applied during the entire sequence of NMR imaging pulse sequences, and magnetic field gradients are used as necessary to encode spatial information into the NMR signal. If a magnetic field gradient within an imaging volume is a function of position, then so is the resonance frequency $\omega$. In fact, if the imaging gradient is linear, the resulting frequency spectrum is a one-dimensional projection of the NMR signal distribution along the direction of the gradient.

Referring now to the basic NMR pulse sequence of FIG. 2, in addition to FIG. 1, the selective excitation pulse sequence is described. Selection of thin planar slab 102 and the excitation of nuclear spins therein is discussed first beginning with interval $q_1$ as shown along horizontal time axis 106 in FIG. 2. During interval $q_1$, imaging sample 100 is subjected to positive magnetic field gradient $G_z$ so that sample 100 is influenced by a total magnetic field in the Z-axis direction composed of the static magnetic field $B_0$ and the magnetic field gradient $G_z$. The $G_z$ gradient is constant throughout the imaging volume but has a time dependent magnitude denoted by $G_z(t) = \alpha \beta_z / \alpha z$. This is shown as the positive going waveform 108. At the approximate mid-point of time interval $q_1$, sample 100 is subjected to a selective 90° RF pulse as shown on the RF axis. The frequency content of the 90° RF pulse is selected so as to preferentially excite nuclear spins in a thin slab 102, in which the precession frequency $\omega$ is as predicted by equation (1). Nuclear spins outside region 102 remain substantially unaffected by the RF pulse. The spatially "selective" nature of the 90° RF pulse is thus apparent.

The 90° RF pulse is preferably a carrier frequency signal (at the precession frequency) which is amplitude modulated by sinc (bt)=(sin bt)/bt, in which t is time and b is a constant, which produces a substantially rectangular thickness profile for thin planar slab 102. Alternatively, other frequency selective 90° RF pulses can be used, providing the resulting thin planar slab 102 has a substantially rectangular profile.

At the end of interval $q_1$, nuclear spins in thin slab 102 have been reoriented (nutated, or flipped) into the x-y plane. Although the nutated spins precess at the same frequency given by equation (1) above, they progressively become out of phase with one another due to the dephasing effects of the $G_z$ gradient during the second half of interval $q_1$. The nuclear spins can be rephased by the application in interval $q_2$ of a negative $G_z$ gradient shown as the negative going waveform 110. The positive and negative $G_z$ gradients are selected such that:

$$\int_{q_1} G_z(t)dt = - \int_{q_2} G_z(t)dt \quad (2)$$

in which $\int_{q_1}$ is the integral of the waveform of gradient $G_z(t)$ over interval $q_1$ and $\int_{q_2}$ is the integral of the waveform of gradient $G_z$ over interval $q_2$. This rephasing is done during the interval $q_2$. The NMR signal data are collected during interval $q_3$ by observing the free induction decay (FID) signal in the presence of an applied magnetic field gradient $G_x$ directed along the x-axis direction and shown as the waveform 112. Spatial information from entire planar slab 102 is therefore encoded in the direction of the x gradient.

A more complete treatment of these basic NMR concepts is provided in a recent text edited by Leon Kaufman et al., titled "Nuclear Magnetic Resonance Imaging in Medicine", Igaku-Shoin, New York and Tokyo (1981); and also in an earlier text by Thomas C. Farrar et al. titled "Pulse and Fourier Transform NMR, An Introduction to Theory and Methods", Academic Press, New York (1971). Accordingly, reference is now made herein to these sources for more detailed descriptions of the various common NMR techniques discussed herein.

Referring now to FIGS. 3A and 3B, the results of the selective excitation and x-axis encoding steps are seen. The FID signal of interval $q_3$ of FIG. 2 is shown in slightly more detail in FIG. 3A as comprised of a distribution of Larmor frequencies of various amplitudes resulting from the linear gradient along the x-axis wherein all of the signals have originated in thin slab 102. This composite signal is readily time-sampled, digitized, and subjected to Fourier transformation. This process transforms the NMR FID signal data from the composite respresenting signal strength versus time of FIG. 3A into a curve representing spectral amplitude versus frequency in FIG. 3B. The result is a spectrum that has a shape corresponding to the one-dimensional projection of the strength of the NMR signal onto the frequency axis 114. Had the linear gradient in interval $q_3$ been applied along the y-axis instead of the x-axis, the resulting projection would have reflected the spin density projection as spatially distributed along the y-axis. In a homogeneous sample with symmetry around both x and y-axes, the transformed spectrum would be identical and therefore indistinguishable. However, as shown below with particular reference to the text relevant to FIG. 7 and FIGS. 7A–7H, a heterogeneous sample will not exhibit this symmetry and preferential transaxial dimensions may be advantageously employed.

Beyond the basic NMR imaging method described above, it has been found that significantly enhanced images of liquids moving in heterogeneous tissue samples are produced by using various combinations of unique NMR pulse sequences, and appropriate NMR signal data processing. It has further been found that the NMR methods of the present invention provide a unique means for carrying out non-invasive, in vivo arteriographic studies, but with the added feature that blood flow within the lumen of the vessels can be imaged via a gray scale level directly corresponding to modulation by blood motion. Additionally, the NMR method of the present invention provides a means for discriminating against surrounding stationary tissue so that blood vessel pathways or networks are shown with high contrast. Alternatively stated, a two-dimensional intensity modulated map may be made for in vivo blood flow within a selected portion of the body wherein the blood flow paths are clearly distinguishable relative to the surrounding stationary media, and wherein blood flow rate may be depicted via corresponding gray scale levels.

Figure 5:
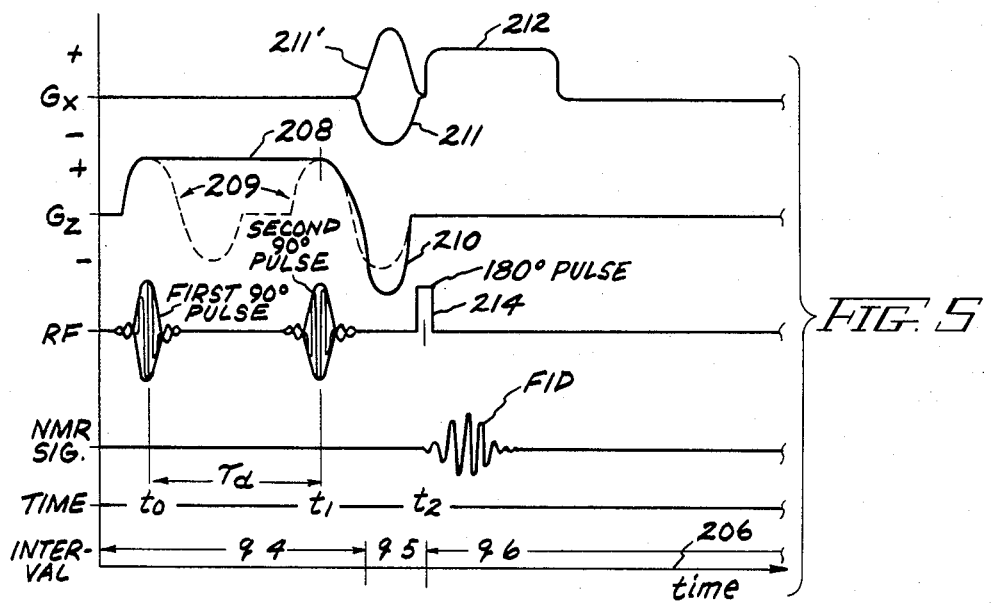
FIG. 5 shows a 90°:90°:180° NMR pulse sequence according to the present invention.

In a preferred embodiment of the present invention, enhanced contrast blood flow imaging is accomplished using the combination of a particular NMR pulse sequence, and a compatible NMR signal processing method which combine to discriminate against stationary objects. Referring now to FIGS. 4A and 4B there are shown side and end views respectively of heterogeneous sample 200 positioned in a static homogeneous magnetic field $B_0$. For all practical purposes, FIG. 4A is completely analogous to the arrangement of FIG. 1 but the view has been altered slightly to provide a clearer exposition. (For mere convenience of description there has been an inconsequential change in orientation, and in the "right handedness" of the x and y-axes of the coordinate system shown in FIG. 1.) As before, sample 200 is cylindrical and has its central axis 204 coincident with the z-axis of a Cartesian coordinate system (the coordinate system may be viewed as rotating about the z-axis at the Larmor frequency) along which the static magnetic field $B_0$ is also directed. In this case, sample 200 may be considered as an idealized longitudinal portion of an arm or a leg having a single blood vessel 218 running along its length. Major arteries and veins tend to run lengthwise of the torso or limbs and thus the z dimension is preferred for one of the two dimensions of the image to be assembled and displayed. The other dimension can be any desired transaxial dimension. In the present illustration, it is chosen to be the X dimension. A predetermined length L of the body portion defines the extent of the region which is to be imaged. Blood flow at a particular instantaneous velocity is entering artery 218 from the left as indicated by flow arrow "$BF_i$" and is leaving from the right as indicated by the flow arrow "$BF_o$". Blood velocities in major arteries typically fall within the range of from 10 to 50 cm/sec, with 30 cm/sec used herein as a nominal mid-range average value. As the position of thin planar slab $\Delta Z$ is progressively moved by linear scanning across length L of sample 200, all of the necessary NMR signal data is collected to allow a complete two-dimensional plan view (alternatively referred to as "scout view") image to be produced. If the thickness of the planar slab, as determined by the shape of the envelope of the 90° selective pulse, is selected as $\Delta Z$ mm and the total length to be imaged is L mm, then it will require no less than N (N=L/$\Delta Z$) distinct, contiguous $\Delta Z$ positions to image sample 200. For any one particular position of the slab $\Delta Z$, an NMR pulse sequence, such as is shown in FIG. 5, is used to provide NMR signal data for the desired blood flow enhanced image. Both contiguous and overlapping positioning of the $\Delta Z$ slab are contemplated herein.

The projection sequence of FIG. 5 starts in time interval $q_4$ with a first 90° selective RF pulse applied nominally at time $t_0$, concurrent with positive magnetic gradient $G_z$ shown by waveform 208. As before, the frequency content of this first 90° selective RF pulse is chosen so as to preferentially excite the nuclear spins in thin slab 202, while sample 200 is subjected to the total magnetic field along the z-axis composed of the static field $B_0$ and the linear magnetic field gradient $G_z$. The center frequency of this pulse determines the particular position along the z-axis at which the slab $\Delta Z$ is located, and the envelope of the pulse determines the thickness and profile of the slab $\Delta Z$. Experience indicates that the linearity of the grey scale modulation of the blood flow image is improved using a sinc (bt) envelope for the two 90° selective pulses due to the minimizing of image blurring along the z dimension resulting from combining non-rectangular slice data. The first 90° selective pulse is followed by a delay of $\tau_d$ seconds, chosen such that blood flow in artery 218 causes a complete exchange of blood in disk shaped volume 202. Considering, for example, that a nominal blood velocity of 30 cm/sec exists and that a slab thickness $\Delta Z$ of 10 mm has been chosen, it would require a delay time $\tau_d$ of 1/30 of a second to assure this complete exchange of blood in volume 202. Following the delay of $\tau_d$ seconds, a second 90° selective RF pulse is applied nominally at time $t_1$. It is advantageous to maintain gradient field $G_z$ (as shown via waveform 208) continuously on during this entire interval. The continuing presence of this gradient thoroughly dephases the spins excited by the first 90° selective pulse (due the effects of $T_2^*$) so that substantially all of the subsequent resulting NMR signal will come from the second 90° selective pulse exciting the non-saturated spins of the blood which has moved into volume 202 during the time $\tau_d$. The dephasing effects of the $G_z$ gradient during the latter portion of the interval $q_4$ (after time $t_1$) are compensated for as before by the application in interval $q_5$ of the negative $G_z$ gradient shown as negative-going waveform 210. The NMR signal data for the particular z location are collected during interval $q_6$ by observing the FID signal in the presence of the applied magnetic field gradient $G_x$ (as before) as shown by waveform 212. The x-axis gradient waveform 212 may be preceded by dephasing compensating waveform 211.

The NMR signal data collected during the N positions of $\Delta Z$ are Fourier transformed into the frequency domain as before, which data may then be assembled into a two-dimensional map of sample 200. Note that entire sample 200 will have been imaged into an x-z plane, and also that for the most part the blood flow paths are the only volumes which produce useful signal strength. Thus, the two-dimensional image provides an intensity modulated plan view of sample 200 with enhanced display of the blood flow networks (arteries and/or veins) as exemplified by the simple sample with single artery 218.

A number of variations in the waveforms used to implement the above NMR pulse sequence may also be used. These variations either offer signal quality or amplitude advantages under certain circumstances, or offer convenience in implementation. The $G_z$ gradient waveform 208 may be comprised of two separate waveforms each effective during a 90° selective pulse, and each with its own dephasing lobe as shown by dotted line waveform 209. The $G_x$ dephase compensation waveform 211' may be of positive polarity (opposite from that shown for waveform 211) under circumstances when it is advantageous to employ a non-selective 180° RF pulse 214. The 180° pulse 214 improves the NMR signal by assuring that the entire temporal portions are usable, and actually produces a one spin echo signal in lieu of the FID signal as shown. This one spin echo signal would appear in the time interval $q_6$, but slightly delayed in time from the FID signal shown. The full spectrum of this one spin echo signal, especially the early occurring high frequency components, are therefore available for advantageous use.

Figure 6:
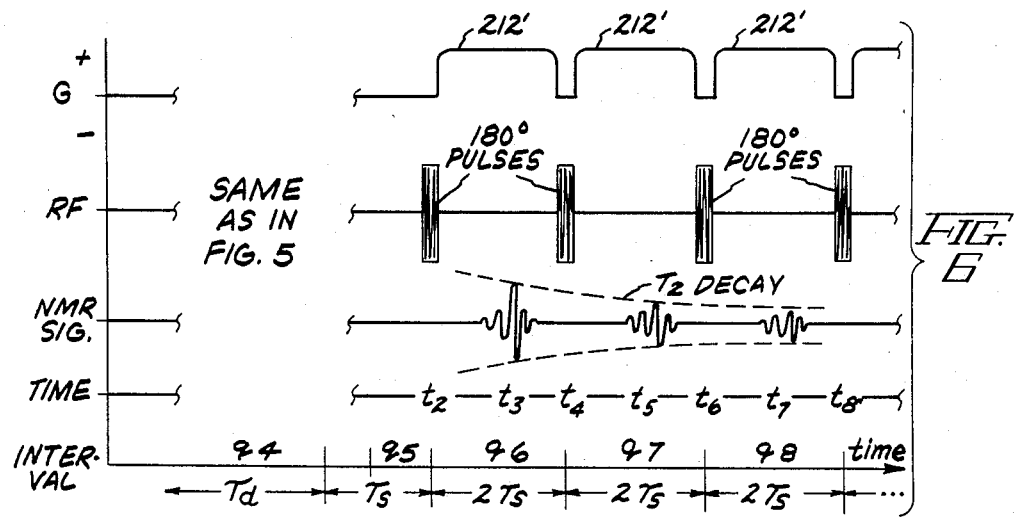
FIG. 6 shows an extension of the NMR pulse sequence of FIG. 5 to include an extended spin echo pulse sequence which complements the previously described pulse sequence.

A blood flow image with an improved signal to noise ratio may be obtained by using an extended NMR spin echo pulse sequence as shown in FIG. 6. FIGS. 5 and 6 are substantially identical for the first two time intervals $q_4$ and $q_5$. Thereafter, in lieu of using the FID signal (or the alternative single spin echo signal) of FIG. 5 to reconstruct the desired image, the multiple spin echo pulse sequences of FIG. 6 are used. At time $t_2$, a 180° non-selective RF pulse is applied to sample 200 which produces a first NMR spin echo signal at time $t_3$, centrally occurring in time interval $q_6$. This signal is spatially encoded by gradient $G_x$ shown by waveform 212'. Subsequent 180° non-selective pulses are applied at times $t_4$, $t_6$, (and thereafter), which produce subsequent NMR spin echo signals at times $t_5$ and $t_7$ (and thereafter) respectively. Conventionally, each of the 180° pulses are spaced $2\tau_s$ seconds apart where $\tau_s$ is the delay time from the second 90° selective pulse to the first 180° non-selective pulse—in accordance with the well known law of equal times. As is clear by the decreasing amplitude of successive spin echo signals, the process is eventually limited by the signal decay time imposed by the transverse relaxation time parameter $T_2$. Even so, the increased signal energy available via the multiple spin echo pulse sequence of FIG. 6 produces a substantially improved signal to noise ratio per pulse projection (alternatively "frame") of NMR data as compared to the single FID signal approach of FIG. 5.

A closely related NMR pulse sequence affords an additional advantage for multiple "frame" averaging of the NMR signal data. This modified sequence uses a 180° change of phase in the two selective 90° pulses. The first +90° selective pulse (at time $t_0$) which operates as previously described is followed in $\tau_d$ seconds by a −90° selective pulse (at time $t_1$). The −90° pulse flips the spins excited by the first +90° pulse back along the z direction, and also flips the new spins brought in by the flowing liquid into volume 202 into the x-y plane where they induce maximum signal into the pick-up coils.

Referring to FIGS. 7 and 8, a typical two-dimensional blood flow image display produced by the method of the present invention is described. FIG. 7 shows an isometric view of a portion of blood-vessel-carrying body member 300. Body member 300 includes small artery 302, larger artery 304, and is oriented relative to a rectangular x-y-z coordinate system as shown. This orientation is identical to the one associated with simpler sample 200 of FIG. 4. Member 300 will, of course, extend, in vivo, well beyond the portion shown, this portion having been selected for blood flow imaging purposes. The relative dimensions are not to scale and the extent and location of the anomalous regions have been exaggerated merely for emphasis. Small artery 302 shows enlarged region 306 as might be illustrative of an aneurysm or the like. A cross-sectional view of member 300 taken through enlargement 306 is shown in FIG. 7E. The lighter shading of region 306 represents a decrease in blood flow velocity often encountered in such regions. Larger artery 304 shows constricted region 308 which may arise from a number of causes, including various schlerotic processes. A cross-sectional view of member 300 taken through constriction 308 is shown in FIG. 7C. The darker shading of region 308 represents an increase in blood flow velocity often encountered in these regions. FIGS. 7A, 7C, 7E and 7G are cross-sectional views of member 300 taken at the locations indicated by the dotted interconnecting lines. All of these cross-sectional views are as observed looking from left to right from the blood inflow direction, along the "$BF_i$" arrows, in the direction of the positive z-axis. When member 300 is subjected to the NMR pulse sequences of the present invention, and the resulting NMR signal data is Fourier transformed as described in connection with FIGS. 3A and 3B, the amplitude versus frequency data of FIGS. 7B, 7D, 7F and 7H are obtained. Corresponding pairings of the various figures are: cross-sectional view 7A pairs with the amplitude/frequency plot of FIG. 7B; FIG. 7C with 7D; FIG. 7E with 7F; and FIG. 7G with 7H.

FIG. 8 depicts a typical CRT display 310 of body member 300 as would be available to a clinician carrying out non-invasive, real time (or near real time) arteriographic blood flow studies made possible by the present invention. The amplitude data of FIGS. 7B, 7D, 7F and 7H are converted into intensity modulated sweeps which are combined side by side to map the blood velocity enhanced NMR data into planar image 312. The two anomalous regions 306' and 308' clearly reflect the blood flow/display intensity correspondence, as well as the spatial extent of the blood flow pathways and the attendant anomaly-related distortions. The CRT display may also include calibration data in the form of gray scale level data in trace 314; and a combined $\Delta Z$ scan velocity compensation signal and display time base linearity trace 316.

The foregoing preferred embodiment presumes a final two-dimensional image assembly using a straightforward collection of successive amplitude/frequency data groups from N continguous slabs $\Delta Z$ in sample 200 or member 300. This is accomplished by carrying out N "slices", each about 10 mm in length for a total sample length of about 20 cm. Hence, N is equal to 20 "slices" for the contiguous slab case. Considering now the effects of varying the scan rates, it is clear that additional signal processing advantages can be obtained by oversampling the object of interest and averaging the signal data in the slices. Complete NMR pulse sequences of either the simple FID type or a spin echo type can typically be completed within 30–70 milliseconds. Assuming that an average complete pulse sequence nominally requires 50 milliseconds, then 20 non-overlapping slices can be completed in approximately 1 second. This appears to imply a fairly fast scanning rate of the $\Delta Z$ slab along the full length L of 20 centimeters per second. In fact, it is advantageous to employ a considerably slower scanning rate in the range of, say 1 to 10 millimeters per second. With a slab thickness $\Delta Z$ of 10 millimeters and the slower scanning rate of 1 millimeter per second, multiple averaging for the NMR signal data in a slice can be achieved. In addition to the potential benefits available from signal level integration, oversampling offers the advantage that the aperture of the system can be shaped by the weighting used in the signal averaging process. For example, if a straightforward running average of the number of data collection sequences made while selected slices pass through a particular point in sample 200, or member 300, is used, the well-known triangular weighted average results. This weighting is much less susceptible to the production of aliasing artifacts than a rectangular aperture equal to the slab thickness $\Delta Z$. If the latter aperture is used with contiguous slices, the basic spatial resolution along the Z-axis is nominally the same as with the running average approach, but the aliasing problem becomes worse.

The foregoing preferred embodiment also presumes that slab $\Delta Z$ is electronically scanned across sample 200, or member 300, by NMR selective excitation along the Z-axis gradient. And the embodiments associated with the descriptions of FIGS. 7 and 8 point out the advantages which may be realized by judicious selection of the parameters—slab thickness; sample length; scan speed; blood flow rate; and NMR pulse sequence time. It is practical in many cases to physically move sample 200, or member 300, through a stationary NMR selective excitation means, and thereby achieve the required full length coverage. Because major arteries and veins tend to run lengthwise in the torso and limbs, significant savings through simplification of the NMR apparatus needed to image an arm or a leg, for example, may be achieved. It would merely be required to transport the body member of interest at the desired velocity for the desired distance in the appropriate region of the NMR magnetic and RF fields as depicted in the illustrative arrangement of FIG. 9.

Figure 9:
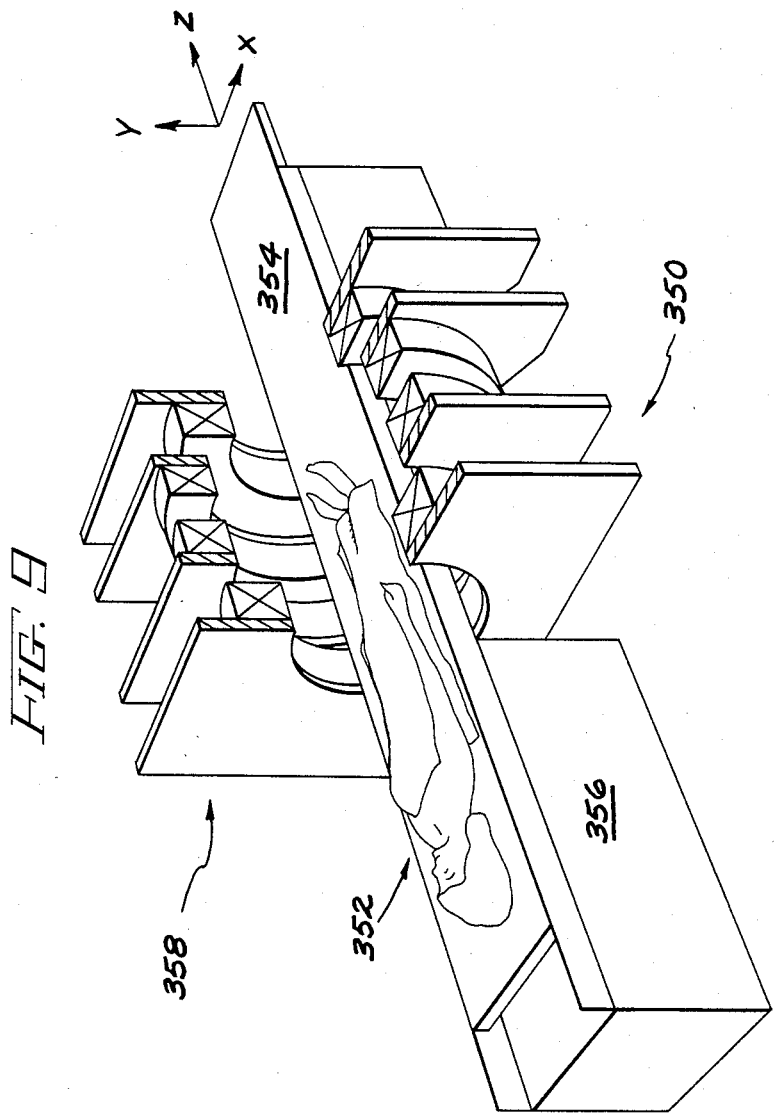
FIG. 9 shows a simplified body member transporting arrangement providing an alternate means of producing the needed relative motion between the body member of interest and the NMR blood flow imaging apparatus.

The body member transporting arrangement 350 of FIG. 9 shows patient 352 being carried on and transported by flat carriage member 354 under control of a servomechanism housed in control and electronics cabinet 356. Electromechanical, pneumatic, or hydraulic servo drive systems may be used to meet the requirements for precisely controlled, smooth translation of patient 352 along the z-axis of the x-y-z coordinate system shown. The NMR coil system is shown as apparatus 358 which includes conventional static and gradient field windings, as well as RF excitation and receiver pick-up windings. Transporting arrangement 350 is fairly versatile in that it allows blood flow imaging study to be readily carried out on one or both of the patient's legs or arms, or selected other portions of the torso. For blood flow studies of more limited extent requiring say, body member translations in the range of 10 to 20 centimeters, the transport arrangement of 350 could be simplified. The patient could be seated in a chair next to the apparatus and the extremity of interest could be secured by and transported in the z-axis direction via a smaller carriage member 354' (not shown), also responsive to the control electronics 356. Ilustrative NMR scanning parameters for a basic embodiment according to the arrangement of FIG. 9 are as follows. Consider that a limited 20 centimeter portion of a patient's arm is to be imaged, and that spatial resolution on the order of a few millimeters is desired. Carriage 354' may be translated at a rate of 5 millimeters per second; a slab thickness $\Delta Z$ of from 2 to 5 millimeters may be selected; a $+90°:-90°:180°$ NMR single spin echo pulse sequence requiring approximately 50 milliseconds may be employed. The resulting real time blood flow imaging of FIG. 8 exemplified by display 310 is realized, thereby materially assisting the clinician's ability to locate and diagnose various diseases, defects or conditions associated with anomalous blood flow.

If the measurement of arterial blood flow is of particular importance, it may then be desirable to compensate for the fact that arterial blood flow is pulsatile. As a result of this aspect of arterial blood flow, the method of the present invention may produce a blood flow image which is modulated by the pulse of the patient's arterial blood flow. That is, arterial blood flow may be indicated as being large for those projections which are coincident with the pulse and low for those projections which are not coincident with the pulse. On the other hand, the venous flow is substantially even and this pulsatile modulation effect is not seen. However, it is possible to mitigate the modulation effects of the pulsating flow by synchronizing the NMR projection measurement with the pulse. Any number of physiological monitoring methods may be employed to produce an electrical pulse signal which may be used to gate the start of the projection measurement described above. In particular, the pulse may be produced electrocardiographically, acoustically or by optical means such as plethysmography.

While the invention has been described in detail herein in accord with certain preferred embodiments thereof, many modifications and changes therein may be effected by those skilled in the art. Accordingly, it is intended by the appended claims to cover all such modifications and changes as fall within the true spirit and scope of the invention.

The invention claimed is:

1. A method for producing a detectable signal for imaging related to the flow rate of fluid moving within one or more confined pathways in an object using NMR pulse sequences, said method comprising the steps of:
   exciting atomic nuclei within a selected planar slab portion of said object by applying a 90° selective RF pulse to said object, said slab being of predetermined thickness and oriented at an angle to each of said pathways respectively;
   exciting atomic nuclei within substantially the same selected planar slab portion a second time after a predetermined time delay by applying a second 90° selective RF pulse to said object said time delay being directly proportional to said slab thickness and inversely proportional to said fluid flow rate so as to generate an NMR signal whose amplitude is related to the quantity of liquid which flowed into the slab via said pathways during said time delay said selective pulses being applied simultaneously with at least one gradient pulse in a direction perpendicular to said planar slab; and
   detecting said NMR signal from said planar slab.

2. A method for generating a detectable signal for imaging related to the flow rate of liquid flowing within one or more confined pathways in a stationary member wherein both the liquid and the surrounding medium are situated within a magnetic field and are composed of nuclei capable of producing NMR signals of comparable magnitudes and using NMR pulse sequences said method comprising the steps of:
   exciting with electromagnetic radiation atomic nuclei within a selected planar slab portion of said member by applying a 90° selective RF pulse to said member, said slab being of predetermined thickness and oriented at an angle to said liquid flow;
   exciting with electromagnetic radiation atomic nuclei within substantially with same selected planar slab portion a second time after a predetermined time delay by applying a second 90° selective RF excitation pulse to said member, said time delay being directly related to said slab thickness and inversely related to the expected liquid flow rate so as to generate an NMR signal whose amplitude is related to the quantity of liquid which has flowed into the slab via said confined pathways during said predetermined time delay said selective pulses being applied simultaneously with at least one gradient pulse in a direction perpendicular to said planar slab;
   detecting said NMR signal from said planar slab; and
   transforming said NMR signal from the time domain into the frequency domain.

3. The method of claim 2 wherein said liquid comprises blood, said pathways comprise blood vessels, and the second selective excitation step is directly followed by the step of applying a 180° non-selective RF pulse to said member to increase the frequency spectral content of said time domain NMR signal.

4. The method of claim 3 wherein said applying step further comprises the steps of applying a series of 180° non-selective RF pulses to said member to produce a corresponding series of spin echo signals so as to increase the frequency spectral content of said time domain NMR spin echo signal.

5. A method for imaging a fluid moving with one or more confined, substantially longitudinal pathways in a body using NMR pulse sequences, said method comprising the steps of:
   (a) positioning said body in a substanially homogeneous magnetic field having a predetermined axis such that said longitudinal pathways are oriented along said preferential axis;
   (b) applying a magnetic gradient field to said body, said gradient configured so as to produce a predetermined distribution of Larmor frequencies along a display axis located wholly within a succession of planar slab portions of said body, said display axis further being oriented at an angle to said preferential axis;
   (c) selectively exciting atomic nuclei within one of said succession of planar slab portions of said body by application of a 90° selective RF pulse to said body, each of said slab portions being of a predetermined thickness, respectively, and oriented at an angle to said preferential axis;
   (d) selectively exciting atomic nuclei within substantially said one planar slab a second time after a time delay proportional to the thickness of said one slab and inversely proportional to the flow rate of said liquid by application of a second 90° selective RF pulse to said body, said selective pulses being applied simultaneously with at least one gradient pulse in a direction perpendicular to said planar slab so as to generate an NMR time domain signal;
   (e) detecting said NMR time domain signal;
   (f) transforming the detected NMR time domain signal into frequency domain data;
   (g) storing said frequency domain data;
   (h) selectively exciting a successive one of said succession of planar slab portions of said body;

(i) repeating steps (c), (d), (e), (f), (g) and (h) for each successive one of said succession of planar slab portions; and (j) compiling said stored data into a two dimensional image by displaying the successively stored frequency domain data as contiguous lines in one dimension of said image.

6. The method of claim 5 wherein said liquid comprises blood, said pathways comprise blood vessels, and said step (h) for each said one of said succession of planar slab portions of said body comprises applying a 180° non-selective RF pulse to said body to produce a corresponding series of spin echo signals so as to increase the frequency spectral content of said NMR spin echo signal.

7. The method of claim 6 in which said step (f) further includes forming a weighted average of the frequency domain data from said spin echoes.

8. The method of claim 5 wherein each one of said succession of planar slab portions of said body is of predetermined thickness and contiguous to the previously selected slab portion.

9. The method of claim 5 wherein each one of said succession of planar slab portions of said body is of predetermined thickness and partially overlapping with the previously selected slab portion.

10. A method for imaging, with enhanced contrast, a fluid moving within one of more confined, substantially longitudinal pathways in a body using NMR pulse sequences, said method comprising the steps of:

(a) positioning said body in a homogeneous magnetic field having a preferential field axis with said longitudinal pathways oriented substantially along said field axis, and transporting said body at a particular rate along said field axis past a fixed excitation slab orthogonal to said field axis;

(b) applying a magnetic gradient field to said body, said gradient configured so as to produce a linear distribution of Larmor frequencies along a display axis located wholly within a succession of planar slab portions of said body, said display axis further being orthogonal to said preferential axis;

(c) selectively exciting atomic nuclei within a first one of a succession of planar slab portions of said body by application of a 90° selective RF pulse to said body, each of said slabs having a predetermined thickness, respectively, and being oriented substantially orthogonally to said pathways and oriented substantially orthogonally to said preferential axis;

(d) selectively exciting atomic nuclei within substantially said one planar slab a second time after a time delay directly proportional to the thickness of said one slab and inversely proportional to the flow rate of said liquid by application of a 90° selective RF pulse to said body, said selective pulses being applied simultaneously with at least one gradient pulse in a direction perpendicular to said slab so as to generate an NMR time domain signal;

(e) detecting said NMR time domain signal;

(f) transforming the detected NMR time domain signal into frequency domain data;

(g) storing said frequency domain data;

(h) selectively exciting a successive one of said succession of planar slab portions of said body transported into said excitation plane;

(i) repeating steps (c), (d), (e), (f), (g) and (h) for each successive one of said succession of planar slab portions; and (j) compiling said stored data into a two dimensional image by displaying the successively stored frequency domain data as contiguous lines in one dimension of said image.

11. The method of claim 10 wherein said liquid comprises blood, said pathways comprise blood vessels, and said step of selectively exciting atomic nuclei within said one planar slab a second time is followed by the step of applying a 180° non-selective RF pulse to said body to increase the frequency spectral content of said time domain NMR signal.

12. The method of claim 10 wherein each one of said succession of planar slab portions of said body is of predetermined thickness and contiguous to the previously selected slab portion.

13. The method of claim 10 wherein each one of said succession of planar slab portions of said body is contiguous to the previously selected slab and oriented substantially orthogonally to said preferential axis.

14. The method of claim 10 wherein each one of said succession of planar slab portions of said body is partially overlapping with the previously selected slab portion.

15. The method of claim 10 further including forming weighted sums of said frequency domain data corresponding to distinct selected slabs.

16. A method for producing two-dimensional images of fluid moving within one or more confined pathways in a body using NMR pulse sequences, said method comprising the steps of:

(a) positioning said body in a homogeneous magnetic field having a preferential axis to produce a net magnetization within said body;

(b) applying a magnetic gradient field to said body, said gradient configured so as to produce a linear distribution of Larmor frequencies along a display axis located wholly within a succession of said planar slab portions of said body, said display axis further being orthogonal to said preferential axis;

(c) selectively exciting atomic nuclei within a first one of a succession of planar slab portions of said body by application of a 90° selective RF pulse to said body, each of said slabs having a predetermined thickness, respectively, and being oriented substantially orthogonally to said pathways and oriented substantially orthogonally to said preferential axis;

(d) selectively exciting atomic muclei within substantially said one planar slab a second time after a time delay directly proportional to the thickness of said one slab and inversely proportional to the flow rate of said liquid by application of a second 90° selective RF pulse to said body, said selective pulses being applied simultaneously with at least one gradient pulse in a direction perpendicular to said planar slab so as to generate an NMR time domain signal;

(e) detecting said NMR time domain signal;

(f) transforming the detected NMR time domain signal into frequency domain data;

(g) storing said frequency domain data;

(h) selectively exciting a successive one of said succession of planar slab portions of said body;

(i) repeating steps (c), (d), (e), (f), (g) and (h) for each successive one of said succession of planar slab portions; and (j) assembling said stored data into a two dimensional image by displaying the successively stored frequency domain data as contiguous lines in one dimension of said image.

17. The method of claim 19 wherein each one of said succession of planar slab portions of said body is contiguous to each successive previously selected slab, and each step of selectively exciting atomic nuclei within the planar slab a second time is directly followed by the step of applying a 180° non-selective RF pulse to said body to increase the frequency spectral content of said time domain NMR signal.

18. The method of claim 16 wherein each one of said succession of planar slab portions of said body is partially overlapping with the previously selected slab portion.

19. The method of claim 16 further including forming weighted sums of said frequency domain data corresponding to distinct selected slabs.

* * * * *